(12) United States Patent
Simpson et al.

(10) Patent No.: US 11,940,438 B2
(45) Date of Patent: Mar. 26, 2024

(54) METHODS AND SYSTEMS FOR MONITORING FUEL QUALITY AND SERVICE ISSUES FOR A POWER SYSTEM USED IN TRANSPORT

(71) Applicant: THERMO KING LLC, Minneapolis, MN (US)

(72) Inventors: John G. Simpson, South St Paul, MN (US); Kyle J. Gleason, Burnsville, MN (US); Randall S. Burnham, St. Michael, MN (US); Arthur H. Ambaruch, Prior Lake, MN (US)

(73) Assignee: THERMO KING LLC, Minneapolis, MN (US)

( * ) Notice: Subject to any disclaimer, the term of this patent is extended or adjusted under 35 U.S.C. 154(b) by 231 days.

(21) Appl. No.: 17/491,138

(22) Filed: Sep. 30, 2021

(65) Prior Publication Data

US 2023/0102325 A1    Mar. 30, 2023

(51) Int. Cl.
*G01N 33/28* (2006.01)
*G07C 5/08* (2006.01)

(52) U.S. Cl.
CPC ....... *G01N 33/2852* (2013.01); *G07C 5/0816* (2013.01)

(58) Field of Classification Search
CPC .............. G07C 5/0816; G01N 33/2852
See application file for complete search history.

(56) References Cited

U.S. PATENT DOCUMENTS

2015/0006059 A1* 1/2015 Castleberry ........ G01N 33/2835
73/61.43

FOREIGN PATENT DOCUMENTS

| CN | 203939579 | 11/2014 |
|---|---|---|
| CN | 209818193 | 12/2019 |
| EP | 2312413 | 4/2011 |
| GB | 2451939 | 2/2009 |
| WO | 2015/057956 | 4/2015 |

OTHER PUBLICATIONS

Extended European Search Report, issued in the corresponding European patent application No. 22198156.6, dated Mar. 2, 2023, 8 pages.

* cited by examiner

*Primary Examiner* — Kevin A Lathers
(74) *Attorney, Agent, or Firm* — Hamre, Schumann, Mueller & Larson, P.C.

(57) ABSTRACT

A method for monitoring fuel quality of a power system used in transport is provided. The method includes a controller of the power system determining that the prime mover is actively running. The method also includes the controller monitoring an output of a water-in-fuel (WIF) sensor configured to measure an amount of water accumulated in a water collection reservoir of a fuel/water separator that separates water from fuel passing there through. Also, the method includes the controller determining an amount of fuel passing through the fuel/water separator. Further, the method includes the controller calculating a fuel quality score of the fuel based on the output of the WIF sensor and the amount of fuel having passed through the fuel/water separator. The method further includes the controller triggering different alerts based on the calculated fuel quality score.

20 Claims, 9 Drawing Sheets

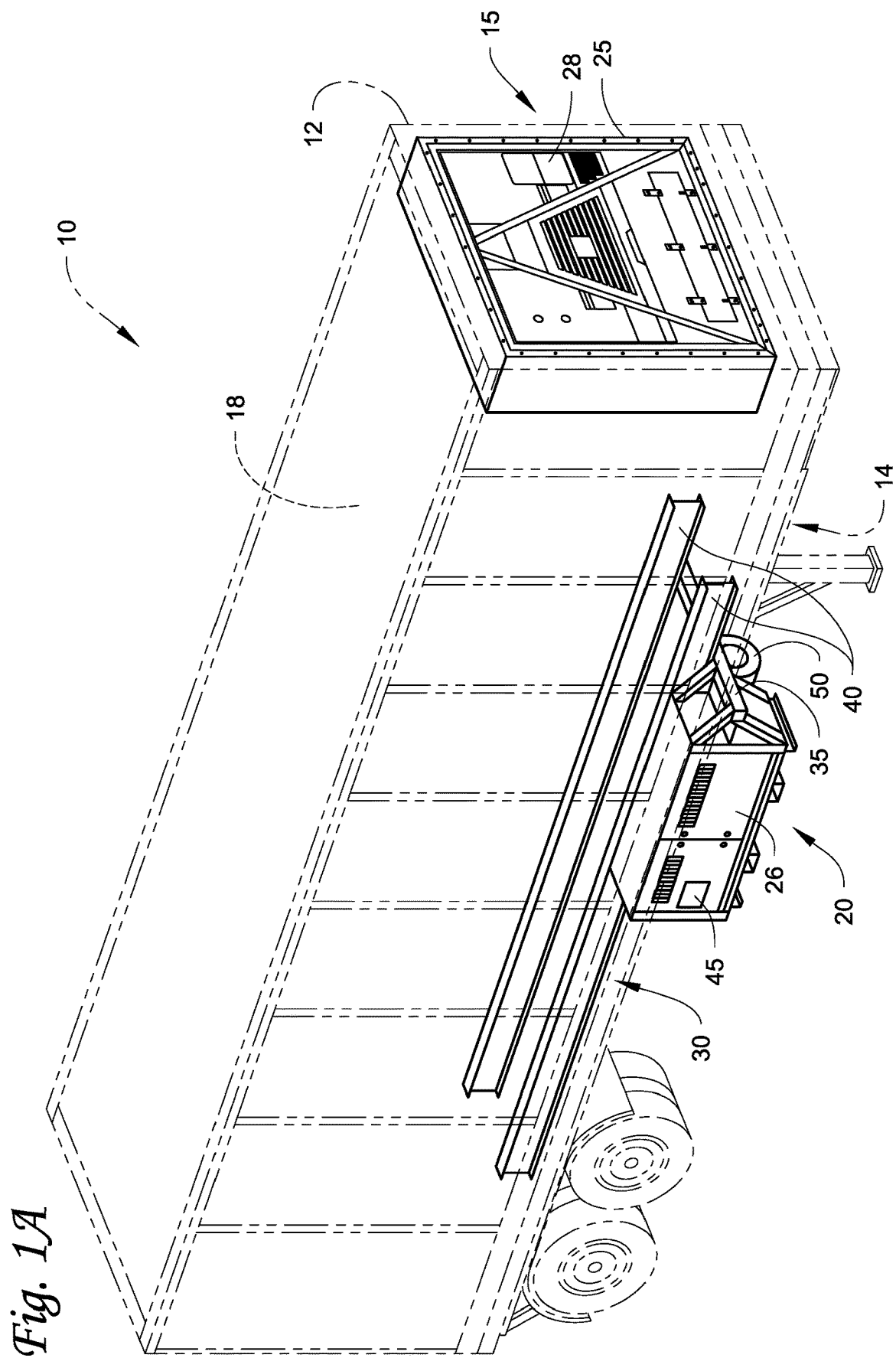

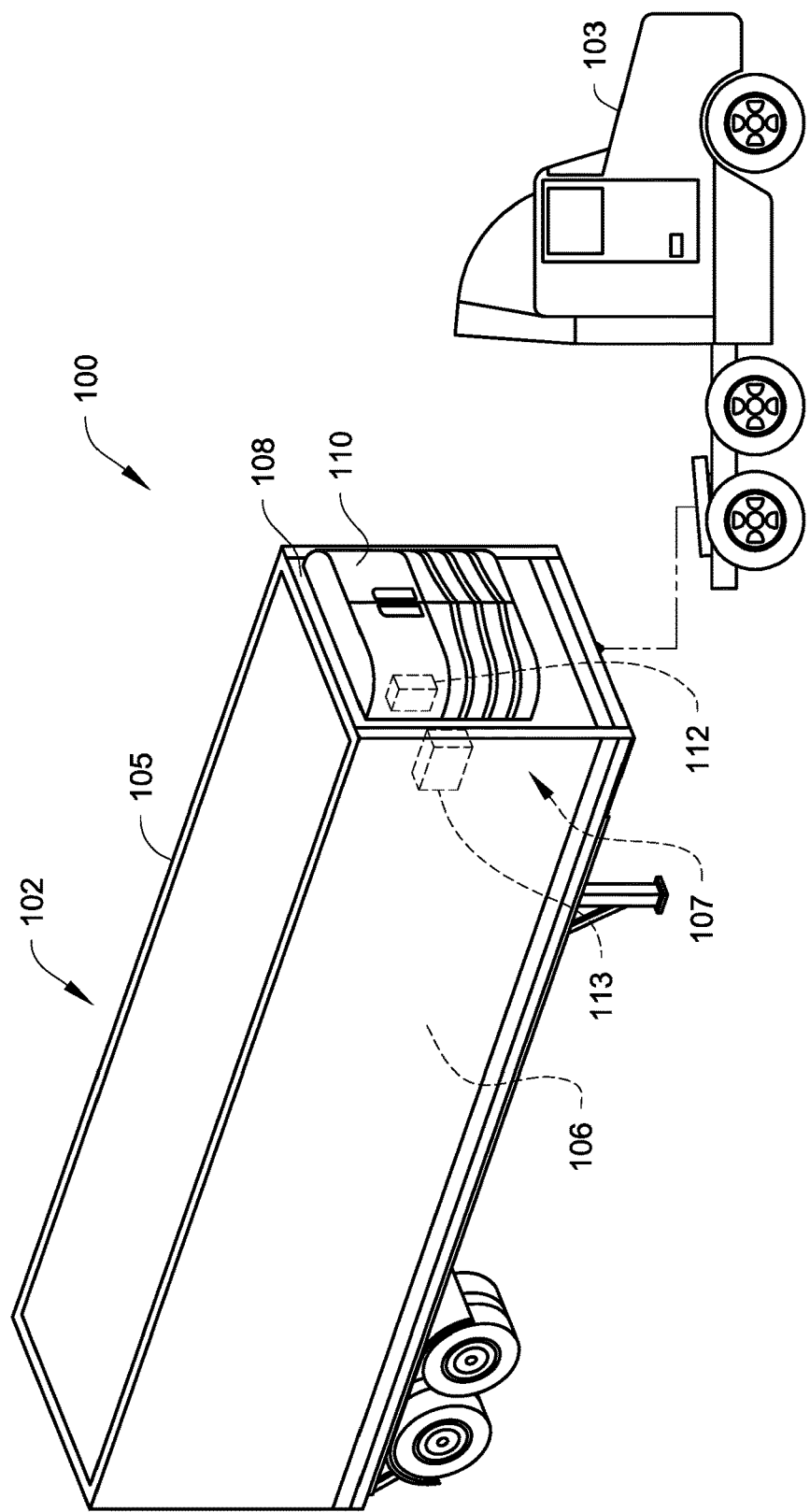

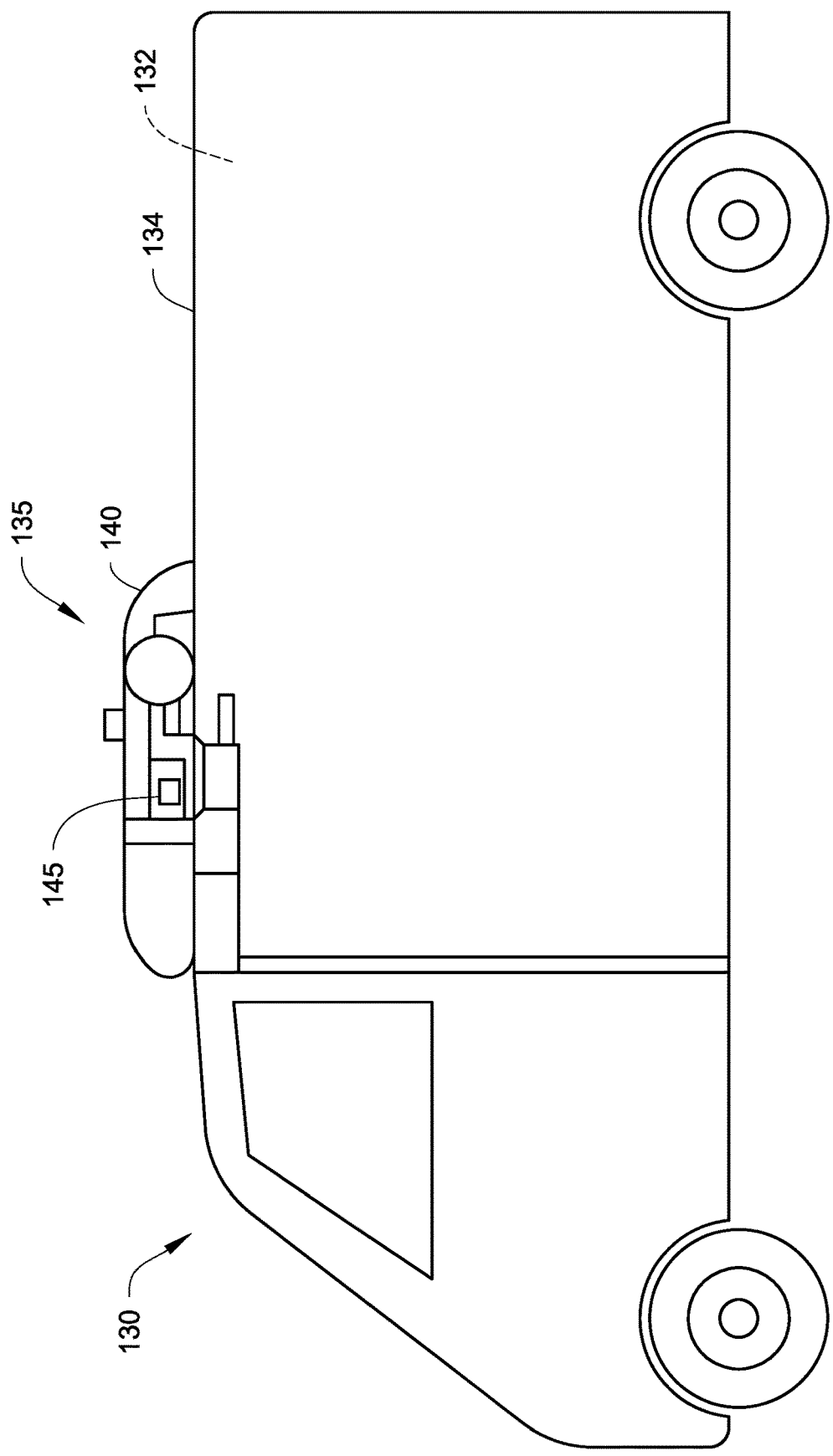

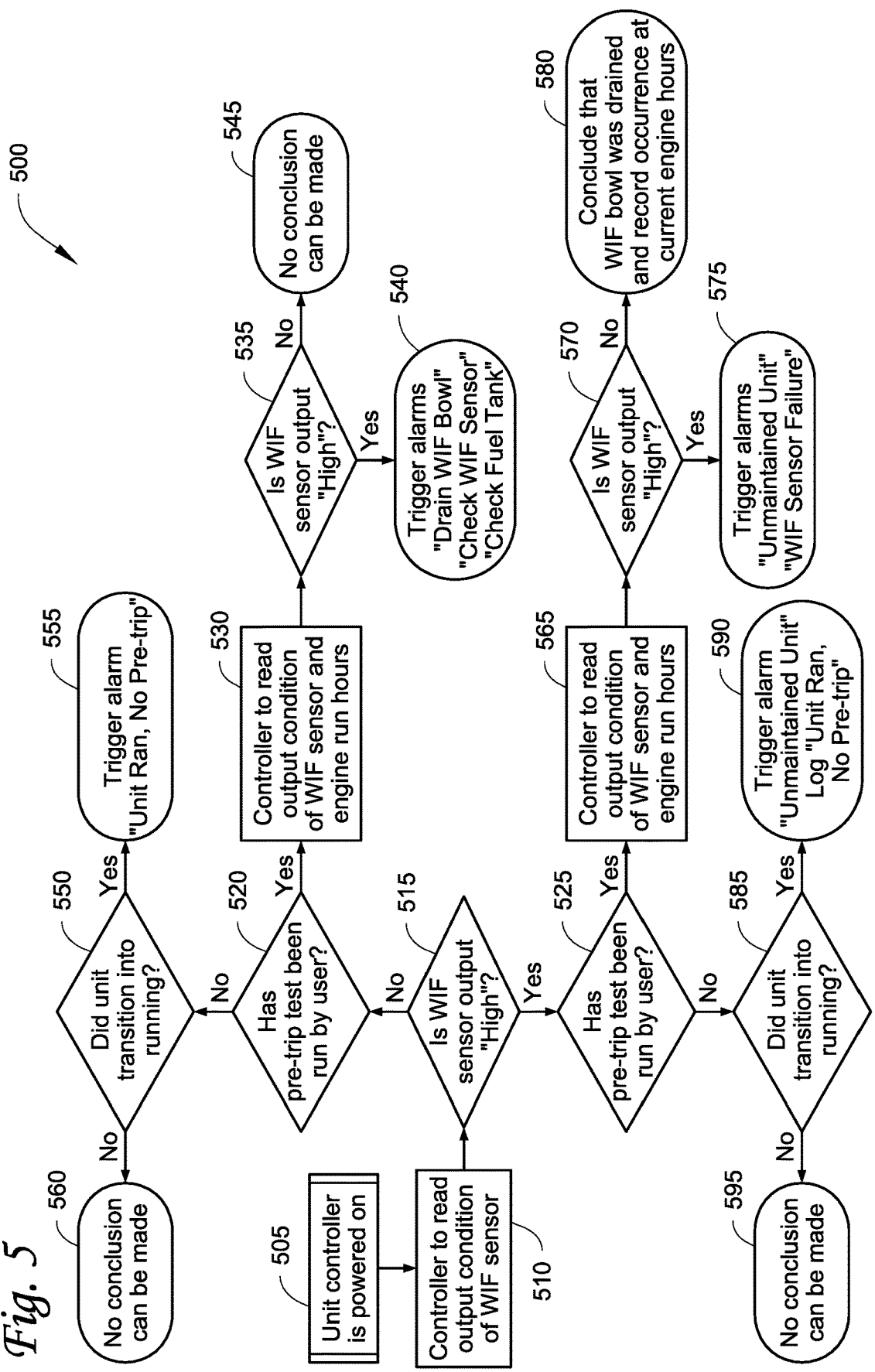

METHODS AND SYSTEMS FOR MONITORING FUEL QUALITY AND SERVICE ISSUES FOR A POWER SYSTEM USED IN TRANSPORT

FIELD

This disclosure relates generally to a power system used to power, for example, a transport climate control system. More specifically, this disclosure relates to methods and systems for monitoring fuel quality and service issues of a fuel system of a power system used in transport.

BACKGROUND

A transport climate control system can include, for example, a transport refrigeration system (TRS) and/or a heating, ventilation and air conditioning (HVAC) system. A TRS is generally used to control an environmental condition (e.g., temperature, humidity, air quality, and the like) within a cargo space of a transport unit (e.g., a truck, a container (such as a container on a flat car, an intermodal container, etc.), a box car, a semi-tractor, a bus, or other similar transport unit). The TRS can maintain environmental condition(s) of the cargo space to maintain cargo (e.g., produce, frozen foods, pharmaceuticals, etc.). In some embodiments, the transport unit can include a HVAC system to control a climate within a passenger space of the vehicle.

A power system can be used to power a transport climate control system, stationary equipment (such as a construction lift), etc. A power system can be used to provide power when a utility power source (e.g., power grid, shore power, etc.) is not available such as, for example, during transport. In some embodiments, the power system can be a generator set ("genset").

Some existing transport units may include a generator set that supplies power to components of the transport climate control system. These generator sets are typically attached directly to the transport unit or transport unit chassis, and include a prime mover to power a generator, as well as a genset controller configured to control operation of the generator set.

SUMMARY

This disclosure relates generally to a power system used to power, for example, a transport climate control system. More specifically, this disclosure relates to methods and systems for monitoring fuel quality and service issues of a fuel system of a power system used in transport.

In particular, the embodiments described herein provide methods and systems for determining and reporting fuel quality issues, a filter condition of a fuel filter (e.g., a fuel/water separator), and adherence to preventative maintenance processes of a fuel system of the power system that is used in transport. Accordingly, the embodiments provided herein can provide an indicator of the condition of the power system and give visibility to measures needed to correct issues prior to power system failure.

It will be appreciated that compression ignition prime movers can have strict limits on the amount of water that can be present in the fuel delivered to and used by the prime mover. If the water content in the fuel is above a prescribed threshold level, performance of the prime mover can be compromised, emissions compliance could be at risk, and potential prime mover damage can occur.

The amount of water in the fuel can be regulated via a filter (e.g., a fuel/water separator). In some embodiments, the filter may require maintenance to keep functioning as intended and may be part of a pre-trip test of the power system. A controller of the power system can monitor the amount of water in the fuel and alert a user if service is required.

The embodiments described herein allows for the ability to track if service procedures are executed properly, if the fuel system (including, for example, a fuel tank of the fuel system) is maintained, and/or if quality fuel (e.g., fuel with a water content that is less than the prescribed threshold level) is being used. In some embodiments, data from the prime mover (e.g., prime mover operation data), data from one or more user inputs (e.g. the user initiating a pre-trip test), and data from a water-in-fuel (WIF) sensor can be used to determine and report fuel quality issues, a filter condition of a fuel filter (e.g., a fuel/water separator), and adherence to preventative maintenance processes of a fuel system of the power system that is used in transport. Access to this data can be used to predict poor service procedures, low quality fuel usage, and needed repair.

The embodiments described herein can use data from a WIF sensor and compare it to a pre-trip test inspection and prime mover run hours to determine the condition of the fuel system of the power system used in transport.

In one embodiment, a method for monitoring fuel quality of a power system used in transport is provided. The method includes a controller of the power system determining that the prime mover is actively running. The method also includes the controller monitoring an output of a WIF sensor configured to measure an amount of water accumulated in a water collection reservoir of a fuel/water separator that separates water from fuel passing there through. Also, the method includes the controller determining an amount of fuel passing through the fuel/water separator. Further, the method includes the controller calculating a fuel quality score of the fuel based on the output of the WIF sensor and the amount of fuel having passed through the fuel/water separator. The method further includes the controller triggering different alerts based on the calculated fuel quality score.

In another embodiment, a power system for use in transport is provided. The power system includes a fuel system that includes: a fuel tank for storing fuel, a fuel/water separator configured to separate water from the fuel as the fuel is being directed to a prime mover of the power system, wherein the fuel/water separator includes a water collection reservoir configured to collect water separated from the fuel by the fuel/water separator, and a WIF sensor configured to measure an amount of the water accumulated in the water collection reservoir. The power system also includes a prime mover and a controller. The prime mover is configured to receive fuel downstream of the fuel/water separator. The controller is configured to control operation of the power system including a speed of the prime mover. The controller is also configured to: determine that the prime mover is actively running, monitor an output of the WIF sensor, determine an amount of fuel passing through the fuel/water separator, calculate a fuel quality score of the fuel based on the output of the WIF sensor and the amount of fuel having passed through the fuel/water separator, and trigger different alerts based on the calculated fuel quality score.

In yet another embodiment, a method for monitoring a service level of a power system used in transport is provided. The method includes a controller of the power system determining that the prime mover has been powered on. The method also includes the controller monitoring an output of a WIF sensor configured to measure an amount of water accumulated in a water collection reservoir of a fuel/water separator that separates water from fuel passing there through. Also, the method includes the controller waiting a predetermined time period after monitoring the output of the WIF sensor. Further, the method includes, after the predetermined time period, the controller determining whether a pre-trip test has been run and obtaining an updated output of the WIF sensor. The method further includes the controller triggering an alert based on the whether the pre-trip test has been urn and the updated output of the WIF sensor.

BRIEF DESCRIPTION OF THE DRAWINGS

References are made to the accompanying drawings that form a part of this disclosure, and which illustrate embodiments in which the systems and methods described in this Specification can be practiced.

FIG. 1A illustrates a perspective view of a container that includes a transport climate control system, according to one embodiment.

FIG. 1B is a perspective view of a refrigerated transport unit attached to a tractor, according to one embodiment.

FIG. 1D is a side view of a van with a transport climate control system, according to one embodiment.

FIG. 5 is a flowchart of a method for monitoring service level of a power system, according to one embodiment.

Like reference numbers represent like parts throughout.

DETAILED DESCRIPTION

Figure 1C:
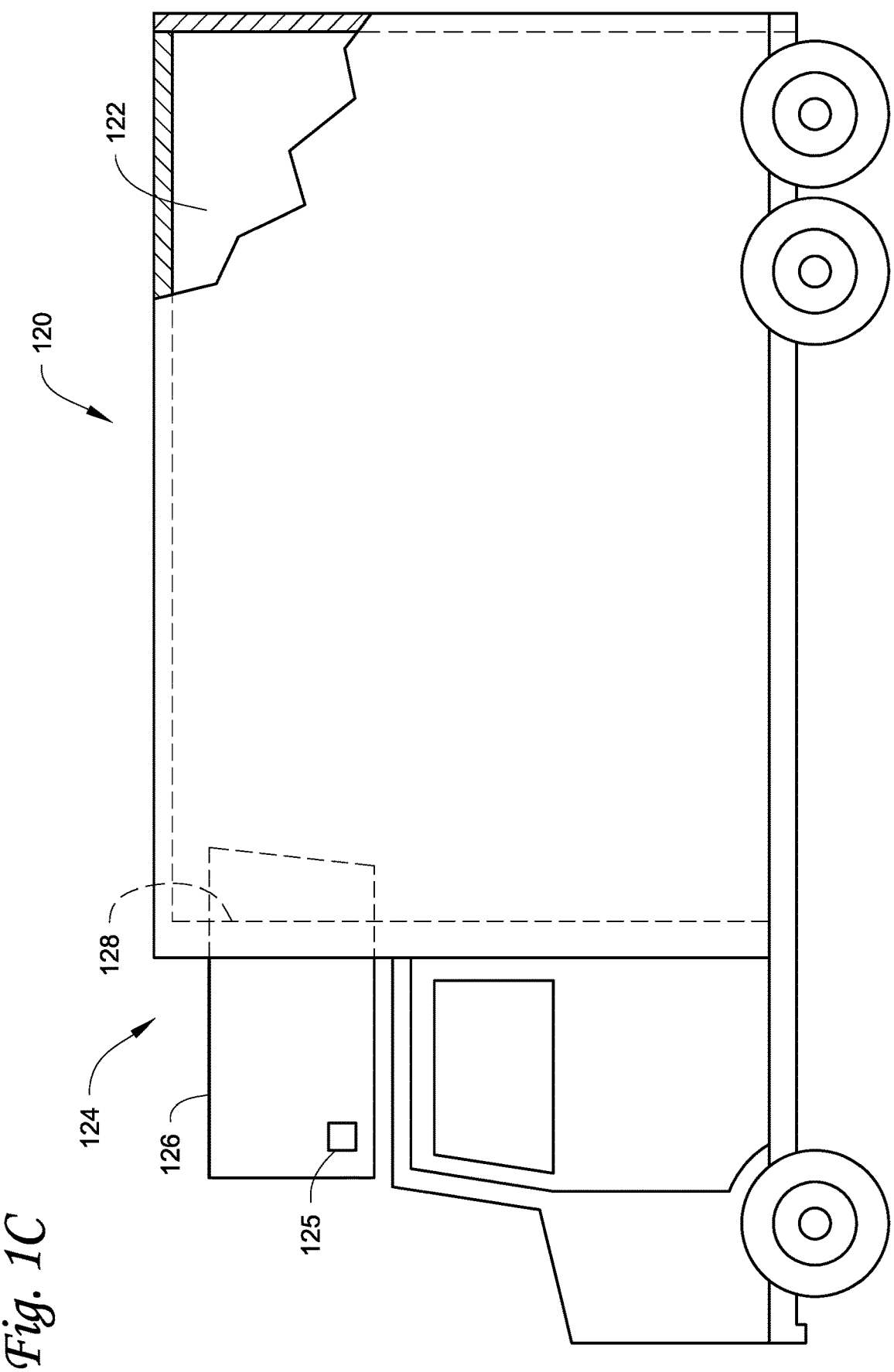
FIG. 1C is a side view of a truck with a transport climate control system, according to one embodiment.

This disclosure relates generally to a power system used to power, for example, a transport climate control system. More specifically, this disclosure relates to methods and systems for monitoring fuel quality and service issues of a fuel system of a power system used in transport.

In some embodiments, the power system can be a generator set. A generator set ("genset") generally includes the combination of a prime mover (e.g., an engine such as an internal combustion engine like a diesel engine) with an electrical machine (e.g., a generator) that can be used to generate electrical power. As described in more detail below, a generator set can also include a battery source that can also be used to generate electrical power. A genset can be used to power one or more loads (e.g., a transport climate control system) when a utility power source is unavailable.

A transport climate control system is generally used to control one or more environmental conditions such as, but not limited to, temperature, humidity, air quality, or combinations thereof, of a transport unit. Examples of transport units include, but are not limited to a truck, a container (such as a container on a flat car, an intermodal container, a marine container, a rail container, etc.), a box car, a semi-tractor, a passenger vehicle, or other similar transport unit. A climate controlled transport unit can be used to transport perishable items such as pharmaceuticals, produce, frozen foods, and meat products and/or can be used to provide climate comfort for passengers in a passenger space of a passenger vehicle. The transport climate control system may include a vapor-compressor type climate controlled system, a thermal accumulator type system, or any other suitable climate controlled system that can use a working fluid (e.g., refrigerant, etc.), cold plate technology, or the like.

A transport climate control system can include a climate control unit (CCU) attached to a transport unit to control one or more environmental conditions (e.g., temperature, humidity, air quality, etc.) of a climate controlled space of the climate controlled transport unit. The CCU can include, without limitation, a climate control circuit (including, for example, a compressor, a condenser, an expansion valve, and an evaporator), and one or more fans or blowers to control the heat exchange between the air within the climate controlled space and the ambient air outside of the climate controlled transport unit.

FIGS. 1A-1E show various transport climate control systems. It will be appreciated that the embodiments described herein are not limited to the examples provided below, but can apply to any type of transport unit (e.g., a truck, a container (such as a container on a flat car, an intermodal container, a marine container, etc.), a box car, a semi-tractor, a passenger bus, or other similar transport unit), etc.

FIG. 1A illustrates one embodiment of an intermodal container 10 with a transport climate control system 15 and a power system 20. The intermodal container 10 can be used across different modes of transport including, for example, ship, rail, tractor-trailer, etc.

The transport climate control system 15 includes a climate control unit (CCU) 25 that provides environmental control (e.g. temperature, humidity, air quality, etc.) within a climate controlled space 18 of the intermodal container 10. The climate control system 15 also includes a programmable climate controller 28 and one or more sensors (not shown) that are configured to measure one or more parameters of the climate control system 15 (e.g., an ambient temperature outside of the intermodal container 10, a space temperature within the climate controlled space 18, an ambient humidity outside of the intermodal container 10, a space humidity within the climate controlled space 18, etc.) and communicate parameter data to the climate controller 28.

When operating in a continuous cooling mode and/or a start-stop cooling mode, the transport climate control system 15 can operate in a pulldown setting and in a steady-state setting. The pulldown setting generally occurs when, for example, the climate controlled space 18 is being cooled from an ambient temperature down to a desired set-point temperature so that the transport climate control system 15 can bring the temperature down to the desired set-point temperature as quickly as possible. The steady-state setting generally occurs when, for example, the climate in the climate controlled space 18 has already reached or is close to approaching a desired set-point temperature and the transport climate control system 15 is working to maintain the desired set-point temperature.

The CCU 25 is disposed on a front wall 12 of the intermodal container 10. In other embodiments, it will be appreciated that the CCU 25 can be disposed, for example, on a rooftop or another wall of the intermodal container 10. The CCU 25 includes a transport climate control circuit (not shown) that connects, for example, a compressor, a condenser, an evaporator and an expander (e.g., expansion valve) to provide conditioned air within the climate controlled space 18.

The climate controller 28 may comprise a single integrated control unit or may comprise a distributed network of climate controller elements (not shown). The number of distributed control elements in a given network can depend upon the particular application of the principles described herein. The climate controller 28 is configured to control operation of the climate control system 15 including the transport climate control circuit.

The climate control system 15 is powered by the power system 20 that can distribute power to the climate control system 15 when a utility power source is unavailable. In this embodiment, the power system 20 is a generator set disposed on a bottom wall 14 of the intermodal container 10 and connected to one or more components of the climate control system 15 (e.g., a compressor, one or more fans and/or blowers, the climate controller 28, one or more sensors, etc.).

In this embodiment, the power system 20 includes a housing 26 attached to a frame 30 by a mounting assembly 35. The mounting assembly 35 can extend between the housing 26 and cross members 40 that are part of the frame 30. The mounting assembly 35 can be made of a high-strength material (e.g., steel, etc.) to rigidly attach the power system 20 to the intermodal container 10. The power system 20 includes a power system controller 45 that is configured to control operation of the power system 20.

A fuel tank 50 is also provided and configured to supply fuel to the power system 20. The fuel tank 50 can be part of or separate from the power system 20.

FIG. 1B illustrates one embodiment of a climate controlled transport unit 102 attached to a tractor 103. The climate controlled transport unit 102 includes a climate control system 100 for a transport unit 105. The tractor 103 is attached to and is configured to tow the transport unit 105. The transport unit 105 shown in FIG. 1A is a trailer.

The transport climate control system 100 includes a climate control unit (CCU) 110 that provides environmental control (e.g. temperature, humidity, air quality, etc.) within a climate controlled space 106 of the transport unit 105. The climate control system 100 also includes a programmable climate controller 107 and one or more sensors (not shown) that are configured to measure one or more parameters of the climate control system 100 (e.g., an ambient temperature outside of the transport unit 105, a space temperature within the climate controlled space 106, an ambient humidity outside of the transport unit 105, a space humidity within the climate controlled space 106, etc.) and communicate parameter data to the climate controller 107.

The transport climate control system 100 can operate in multiple operation modes including, for example, a continuous cooling mode, a start/stop cooling mode, a heating mode, a defrost mode, a null mode, etc. When operating in a continuous cooling mode and/or a start-stop cooling mode, the transport climate control system 100 can operate in a pulldown setting and in a steady-state setting. The pulldown setting generally occurs when, for example, the climate controlled space 106 is being cooled from an ambient temperature down to a desired set-point temperature so that the transport climate control system 100 can bring the temperature down to the desired set-point temperature as quickly as possible. The steady-state setting generally occurs when, for example, the climate in the climate controlled space 106 has already reached or is close to approaching a desired set-point temperature and the transport climate control system 100 is working to maintain the desired set-point temperature.

The CCU 110 is disposed on a front wall 108 of the transport unit 105. In other embodiments, it will be appreciated that the CCU 110 can be disposed, for example, on a rooftop or another wall of the transport unit 105. The CCU 110 includes a transport climate control circuit (not shown) that connects, for example, a compressor, a condenser, an evaporator and an expander (e.g., expansion valve) to provide conditioned air within the climate controlled space 106.

The climate controller 107 may comprise a single integrated control unit 112 or may comprise a distributed network of climate controller elements 112, 113. The number of distributed control elements in a given network can depend upon the particular application of the principles described herein. The climate controller 107 is configured to control operation of the climate control system 100 including the transport climate control circuit.

The climate control system 100 is powered by a power system that can distribute power to the climate control system 100 when a utility power source is unavailable. In some embodiments, the power system can be housed within the CCU 110. In some embodiments, the power system can be a generator set (not shown) attached to the transport unit 105 and connected to one or more components of the climate control system 100 (e.g., a compressor, one or more fans and/or blowers, the climate controller 107, one or more sensors, etc.). In some embodiments, a fuel tank (not shown) can be provided for supplying fuel to the power system. The fuel tank can be part of or separate from the power system.

FIG. 1C is a side view of a truck 120 with a transport climate control system 124, according to an embodiment. The truck 120 includes a climate controlled space 122 for carrying cargo. The transport climate control system 124 includes a CCU 126 that is mounted to a front wall 128 of the climate controlled space 122. The CCU 126 can include, among other components, a climate control circuit (not shown) that connects, for example, a compressor, a condenser, an evaporator, and an expander (e.g., expansion valve) to provide climate control within the climate controlled space 122. In an embodiment, the CCU 126 can be a transport refrigeration unit.

The transport climate control system 124 also includes a programmable climate controller 125 and one or more climate control sensors (not shown) that are configured to measure one or more parameters of the transport climate control system 124 (e.g., an ambient temperature outside of the truck 120, an ambient humidity outside of the truck 120, a compressor suction pressure, a compressor discharge pressure, a supply air temperature of air supplied by the CCU 126 into the climate controlled space 122, a return air temperature of air returned from the climate controlled space 122 back to the CCU 126, a humidity within the climate controlled space 122, etc.) and communicate climate control data to the climate controller 125. The one or more climate control sensors can be positioned at various locations outside the truck 120 and/or inside the truck 120 (including within the climate controlled space 122).

The transport climate control system 124 can operate in multiple operation modes including, for example, a continuous cooling mode, a start/stop cooling mode, a heating mode, a defrost mode, a null mode, etc. When operating in a continuous cooling mode and/or a start-stop cooling mode, the transport climate control system 124 can operate in a pulldown setting and in a steady-state setting. The pulldown setting generally occurs when, for example, the climate controlled space 122 is being cooled from an ambient temperature down to a desired set-point temperature so that the transport climate control system 124 can bring the temperature down to the desired set-point temperature as quickly as possible. The steady-state setting generally occurs when, for example, the climate in the climate controlled space 122 has already reached or is close to approaching a desired set-point temperature and the transport climate control system 124 is working to maintain the desired set-point temperature.

The climate controller 125 is configured to control operation of the transport climate control system 124 including components of the climate control circuit. The climate controller 125 may include a single integrated control unit or may include a distributed network of climate controller elements (not shown). The number of distributed control elements in a given network can depend upon the particular application of the principles described herein. The measured parameters obtained by the one or more climate control sensors can be used by the climate controller 125 to control operation of the climate control system 124.

The climate control system 124 is powered by a power system that can distribute power to the climate control system 124 when a utility power source is unavailable. In some embodiments, the power system can be housed within the CCU 126. In some embodiments, the power system can be housed within the truck 120 and connected to one or more components of the climate control system 124 (e.g., a compressor, one or more fans and/or blowers, the climate controller 145, one or more sensors, etc.). In some embodiments, the power system can be a generator set (not shown) attached to the truck 120 and connected to one or more components of the climate control system 124 (e.g., a compressor, one or more fans and/or blowers, the climate controller 125, one or more sensors, etc.). In some embodiments, a fuel tank (not shown) can be provided for supplying fuel to the power system. The fuel tank can be part of or separate from the power system.

FIG. 1D depicts a side view of a van 130 with a transport climate control system 135 for providing climate control within a climate controlled space 132, according to one embodiment. The transport climate control system 135 includes a climate control unit (CCU) 140 that is mounted to a rooftop 134 of the van 130. In an embodiment, the CCU 140 can be a transport refrigeration unit. The climate control system 135 also includes a programmable climate controller 145 and one or more sensors (not shown) that are configured to measure one or more parameters of the climate control system 135 (e.g., an ambient temperature outside of the van 130, a space temperature within the climate controlled space 132, an ambient humidity outside of the van 130, a space humidity within the climate controlled space 132, etc.) and communicate parameter data to the climate controller 145.

The transport climate control system 135 can include, among other components, a transport climate control circuit (not shown) that connects, for example, a compressor, a condenser, an evaporator, and an expander (e.g., an expansion valve) to provide climate control within the climate controlled space 132.

The transport climate control system 135 can operate in multiple operation modes including, for example, a continuous cooling mode, a start/stop cooling mode, a heating mode, a defrost mode, a null mode, etc. When operating in a continuous cooling mode and/or a start-stop cooling mode, the transport climate control system 135 can operate in a pulldown setting and in a steady-state setting. The pulldown setting generally occurs when, for example, the climate controlled space 132 is being cooled from an ambient temperature down to a desired set-point temperature so that the transport climate control system 135 can bring the temperature down to the desired set-point temperature as quickly as possible. The steady-state setting generally occurs when, for example, the climate in the climate controlled space 132 has already reached or is close to approaching a desired set-point temperature and the transport climate control system 135 is working to maintain the desired set-point temperature.

The climate controller 145 may comprise a single integrated control unit or may comprise a distributed network of climate controller elements (not shown). The number of distributed control elements in a given network can depend upon the particular application of the principles described herein. The climate controller 145 is configured to control operation of the climate control system 135 including the transport climate control circuit.

The climate control system 135 is powered by a power system that can distribute power to the climate control system 135 when a utility power source is unavailable. In some embodiments, the power system can be housed within the CCU 140. In some embodiments, the power system can be housed within the van 130 and connected to one or more components of the climate control system 135 (e.g., a compressor, one or more fans and/or blowers, the climate controller 145, one or more sensors, etc.). In some embodiments, the power system can be a generator set (not shown) attached to the van 130 and connected to one or more components of the climate control system 135 (e.g., a compressor, one or more fans and/or blowers, the climate controller 145, one or more sensors, etc.). In some embodiments, a fuel tank (not shown) can be provided for supplying fuel to the power system. The fuel tank can be part of or separate from the power system.

Figure 1E:
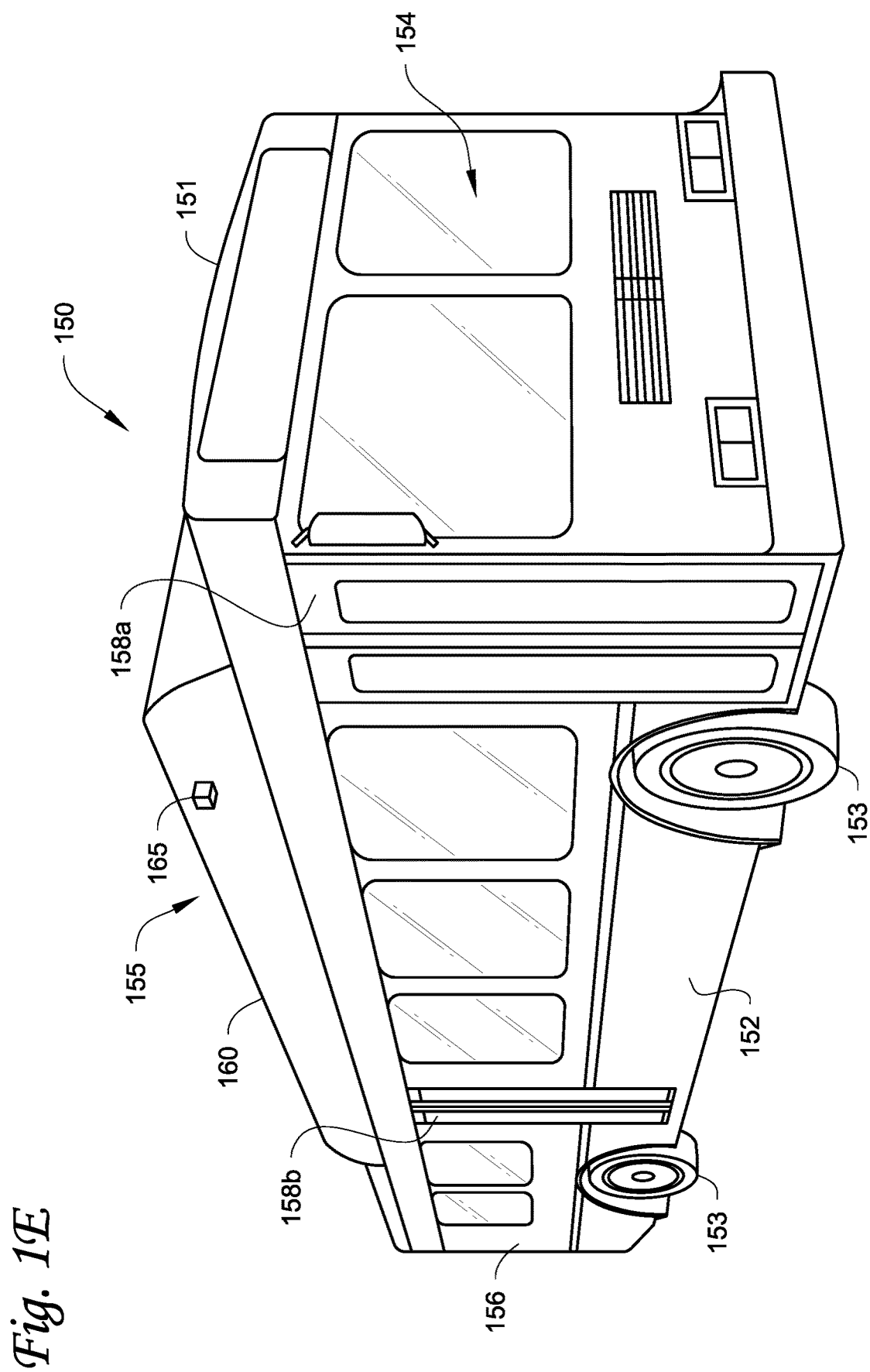
FIG. 1E is a perspective view of a passenger vehicle including a climate control system, according to one embodiment.

FIG. 1E is a perspective view of a passenger vehicle 150 including a transport climate control system 155, according to one embodiment. In the embodiment illustrated in FIG. 1E, the passenger vehicle 150 is a mass-transit bus that can carry passenger(s) (not shown) to one or more destinations. In other embodiments, the passenger vehicle 150 can be a school bus, railway vehicle, subway car, or other commercial vehicle that carries passengers. Hereinafter, the term "vehicle" shall be used to represent all such passenger vehicles, and should not be construed to limit the scope of the application solely to mass-transit buses. The transport climate control system 155 can provide climate control within a climate controlled space which in this embodiment is a passenger compartment 154.

The passenger vehicle 150 includes a frame 152, a passenger compartment 154 supported by the frame 152, wheels 153, and a compartment 156. The frame 152 includes doors 158 that are positioned on a side of the passenger vehicle 150. A first door 158a is located adjacent to a forward end of the passenger vehicle 150, and a second door 158b is positioned on the frame 152 toward a rearward end of the passenger vehicle 150. Each door 158 is movable between an open position and a closed position to selectively allow access to the passenger compartment 154.

The transport climate control system 155 includes a climate control unit (CCU) 160 that is mounted to a rooftop 151 of the passenger vehicle 150. In an embodiment, the CCU 160 can be a HVAC unit. The climate control system 155 also includes a programmable climate controller 165 and one or more sensors (not shown) that are configured to measure one or more parameters of the transport climate control system 155 (e.g., an ambient temperature outside of the passenger vehicle 150, a space temperature within the passenger compartment 154, an ambient humidity outside of the passenger vehicle 150, a space humidity within the passenger compartment 154, etc.) and communicate parameter data to the climate controller 165.

The transport climate control system 155 can include, among other components, a transport climate control circuit (not shown) that connects, for example, a compressor, a condenser, an evaporator, and an expander (e.g., an expansion valve) to provide climate control within the passenger compartment 154.

The transport climate control system 155 can operate in multiple operation modes including, for example, a continuous cooling mode, a start/stop cooling mode, a heating mode, a defrost mode, a null mode, etc. When operating in a continuous cooling mode and/or a start-stop cooling mode, the transport climate control system 155 can operate in a pulldown setting and in a steady-state setting. The pulldown setting generally occurs when, for example, the passenger compartment 154 is being cooled from an ambient temperature down to a desired set-point temperature so that the transport climate control system 155 can bring the temperature down to the desired set-point temperature as quickly as possible. The steady-state setting generally occurs when, for example, the climate in the passenger compartment 154 has already reached or is close to approaching a desired set-point temperature and the transport climate control system 155 is working to maintain the desired set-point temperature.

The climate controller 165 may comprise a single integrated control unit or may comprise a distributed network of climate controller elements (not shown). The number of distributed control elements in a given network can depend upon the particular application of the principles described herein. The climate controller 165 is configured to control operation of the climate control system 155 including the transport climate control circuit.

The climate control system 135 is powered by a power system that can distribute power to the climate control system 135 when a utility power source is unavailable. In some embodiments, the power system can be housed within the CCU 160. In some embodiments, the power system can be housed within the vehicle 150 and connected to one or more components of the climate control system 155 (e.g., a compressor, one or more fans and/or blowers, the climate controller 165, one or more sensors, etc.). In some embodiments, the power system can be a generator set (not shown) attached to the passenger vehicle 150 and connected to one or more components of the climate control system 155 (e.g., a compressor, one or more fans and/or blowers, the climate controller 165, one or more sensors, etc.). In some embodiments, a fuel tank (not shown) can be provided for supplying fuel to the power system. The fuel tank can be part of or separate from the power system.

The compartment 156 is located adjacent the rear end of the passenger vehicle 150, can include the power system. In some embodiments, the compartment 156 can be located at other locations on the vehicle 150 (e.g., adjacent the forward end, etc.).

Figure 2:
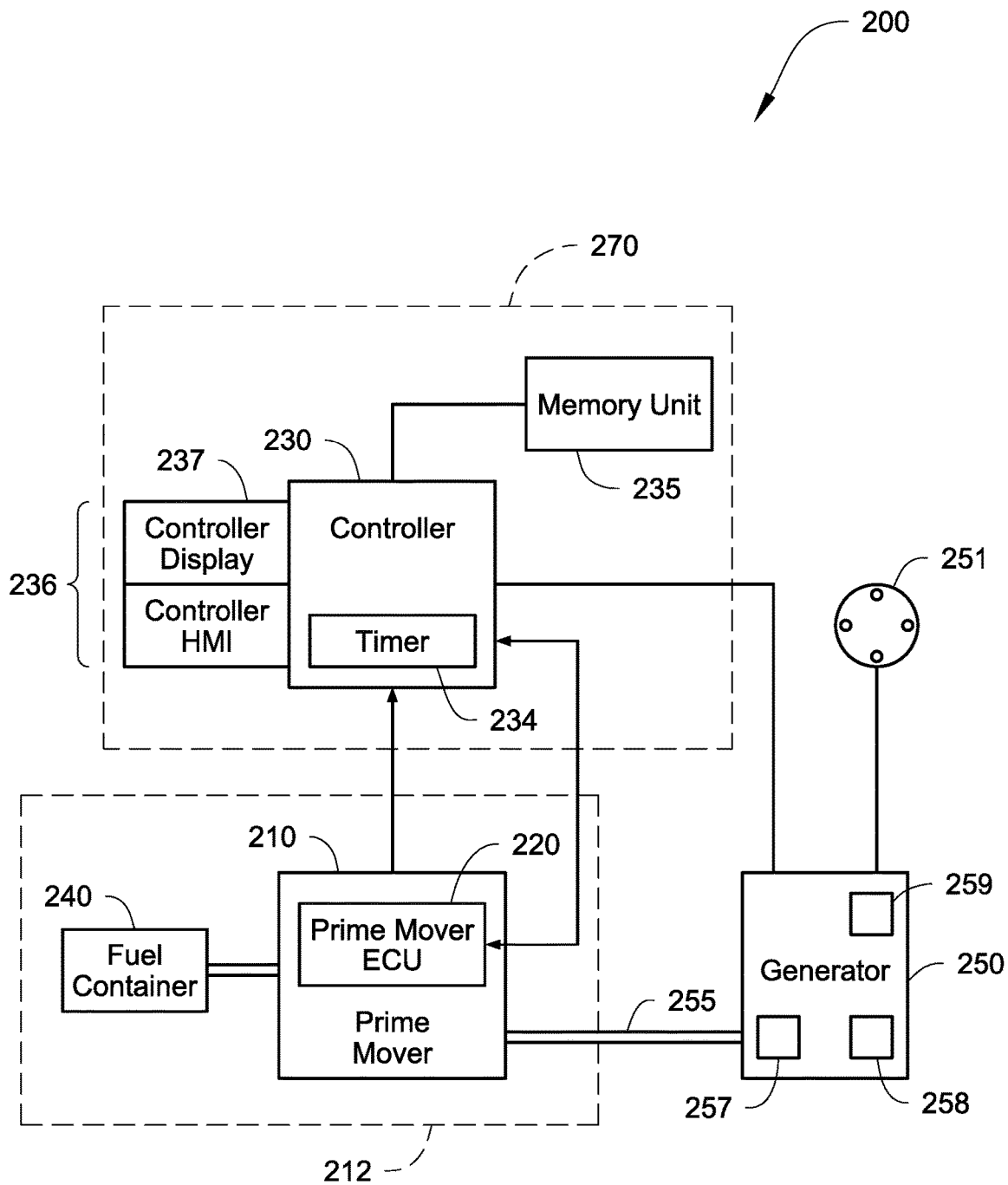
FIG. 2 is a schematic diagram of a power system, according to one embodiment.

FIG. 2 illustrates a schematic view of an embodiment of a power system that is a generator set 200. The power system may be configured to provide power to a transport climate control system, such as the transport climate control systems 15, 100, 124, 135, 155 as shown in FIGS. 1A-E. The generator set 200 generally includes a prime mover 210 with an engine control unit (ECU) 220, a genset controller 230, a fuel tank 240 and a generator 250. In some embodiments, the prime mover 210 may not include the ECU 220. The generator set 200 (or portions thereof) can be disposed in the housing 26 as shown in FIG. 1A. The prime mover 210 with the fuel tank 240 together form a fuel system 212. One embodiment of the fuel system 212 is described below with respect to FIG. 3.

The illustrated prime mover 210 may be an internal combustion engine (e.g., diesel engine, etc.) that may generally have a cooling system (e.g., water or liquid coolant system), an oil lubrication system, and an electrical system (none shown). An air filtration system (not shown) filters air directed into a combustion chamber (not shown) of the prime mover 210. The prime mover 210 may also be an engine that is configured specifically for a transport climate control system. The fuel tank 240 is in fluid communication with the prime mover 210 to deliver a supply of fuel to the prime mover 210.

The prime mover 210 can be controlled by the ECU 220. The ECU 220 can be configured to regulate an amount of fuel delivered to the prime mover 210 and can be configured to operate the prime mover 210 at least at a first non-zero speed (e.g., high speed) and a second non-zero speed (e.g., low speed). The ECU 220 is configured so that the prime mover 210 can be maintained at least at either the first non-zero speed or the second non-zero speed in a range of prime mover loads on the prime mover 210.

The ECU 220 is coupled with the controller 230. The genset controller 230 is configured to receive information from the ECU 220, and command the ECU 220 to vary the prime mover 210 between the first non-zero speed and the second non-zero speed. In some embodiments, the first non-zero speed can be ~1800 RPM, and the second non-zero speed can be ~1500 RPM. In other embodiments, the first and second non-zero speeds may be different from ~1800 RPM and ~1500 RPM.

A generator 250 can be coupled to the prime mover 210 by a flex disk 255 that transfers mechanical energy from the prime mover 210 to the generator 250. In some embodiments, the generator 250 can also be coupled to the prime mover 210 indirectly by a driving belt. The generator 250 includes a power receptacle 251 that is in electrical communication with, for example, a CCU 25 (as shown in FIG. 1B) via a power cable (not shown) to provide electrical power to the transport climate control system 15.

The generator 250 may be a 3-phase AC generator that generally includes a rotor 257, a stator 258, and a voltage regulator 259. The rotor 257 is coupled to the flex disk 255 such that the prime mover 210 is operable to rotatably drive the rotor 257 at least at the first non-zero speed and the second non-zero speed. The stator 258 is usually a stationary component of the generator 250 that includes magnetic pole pairs (e.g., two pole pairs).

The voltage regulator 259 includes a field voltage and a field current that are generated by a regulation element (not shown) coupled to the voltage regulator 259. In some embodiments, the regulation element may include batteries or other solid-state components that generate a direct current through the voltage regulator 259. The field voltage and the field current define a field excitation. The field excitation of the generator 250 is generally considered a field of the generator 250. The field can be one part of the rotor 257 and the stator 258.

Rotation of the rotor 257 through the magnetic field induces an output current from the generator 250. The induced output current produces an output voltage of the generator 250 that is directed through the power receptacle 251 to the transport climate control system. It is to be noted that other types of generators can be used in place of the generator 250. The generator 250 as described herein is exemplary only.

The generator 250 further includes an output frequency that can be affected by the speed of the prime mover 210 or the field voltage of the generator 250. In some embodiments, the generator 250 can provide a first output frequency (e.g., ~60 Hertz) when the prime mover 210 is operated at the first non-zero speed, and can provide a second output frequency (e.g., ~50 Hertz) when the prime mover 210 is operated at the second non-zero speed. The transport climate control system may be operated at both frequencies.

The output voltage of the generator 250 may be affected by the output frequency. As such, the generator 250 can provide a first output voltage in response to operation of the generator 250 at the first frequency. The generator 250 can provide a second output voltage in response to operation of the generator 250 at the second frequency. For example, when the generator 250 is operated at the first non-zero speed/frequency (e.g., ~1800 rpm/60 Hertz), the first output voltage can be about 460 volts. When the generator 250 is operated at the second non-zero speed/frequency (e.g., ~1500 rpm/50 Hertz), the second output voltage can be about 380 volts. Thus, the speed of the prime mover 210 can affect the frequency and output voltage of the generator 250.

The generator 250 can be configured to provide a relatively constant load capacity that is sufficient to provide power to the transport climate control system under various loads. A load on the generator 250 corresponds to, for example, the cooling demand or load on the transport climate control system (e.g., electrical power needed by the transport climate control system), and is variable in response to changes in the load on the transport climate control system.

The ECU 220 is configured to control the operation of the prime mover 210 and monitor/obtain prime mover operation data. The ECU 220 may have a microprocessor that can communicate with an array of sensors that are configured to obtain prime mover speed, prime mover run hours, oil temperatures, piston positions, etc. By analyzing the readings from the array of sensors, the ECU 220 can obtain the operation data of the prime mover 210. In some embodiments, the ECU 220 can obtain the operation data of the prime mover 210 almost in real-time. The ECU 220 can be, for example, configured to control an injection pump so that an amount of fuel delivered to combustion chambers of the prime mover 210 can be controlled by the ECU 220. By regulating the amount of fuel delivered, the ECU 220 can be configured to maintain the prime move 210 at an operational speed relatively constantly even when the load on the prime mover 210 may change. In the illustrated embodiment as shown in FIG. 2, the ECU 220 is configured so that the ECU 220 can maintain the prime move 210 at least at two relatively constant operational speeds, for example ~1500 RPM and ~1800 RPM.

As described above, the genset controller 230 is coupled with the ECU 220. The couple between the genset controller 230 and the ECU 220 can be a two-way electronic communication system. The ECU 220 can be configured to obtain the prime mover operation data. The ECU 220 can then send the prime mover operation data to the genset controller 230.

The genset controller 230 may have a microprocessor that is configured to make various operating decisions in response to the prime mover operation data received from the ECU 220. The operating decisions generated by the genset controller 230 can then be transmitted back to the ECU 220 via the coupling between the ECU 220 and the controller 230. After receiving the operating decisions transmitted from the genset controller 230, the ECU 220 may then operate the prime mover 210 in accordance with the operating decisions transmitted from the genset controller 230.

FIG. 2 further shows that the genset controller 230 can be configured to be in electrical communication with a timer 234, a memory unit 235, and/or an operator interface 236. The genset controller 230, the timer 234, the memory unit 235 and the operator interface 236 can be incorporated into a controller panel 270.

In some embodiments, the memory unit 235 may be a Random Access Memory ("RAM") that can maintain a data log related to parameters of the prime mover 210 and the generator 250, as a well as other data.

The operator interface 236 includes a controller display 237 and a controller human machine interface (not shown) for viewing and entering commands into the genset controller 230. The timer 234 may separately measure a duration time that the prime mover 210 operates at the first non-zero speed and/or a duration time that the prime mover 210 operates at the second non-zero speed.

In operation, the genset controller 230 and the ECU 220 can work together to operate the prime mover 210. For example, the ECU 220 can be configured to operate/maintain the prime mover 210 at the first non-zero speed or the second non-zero speed that is lower than the first non-zero speed. In some embodiments, for example as shown above, the first non-zero speed can be ~1800 RPM and the second non-zero speed can be ~1500 RPM.

It is to be noted that in some embodiments, the ECU 220 can be configured to transmit values measured by the array of sensors to the genset controller 230. The genset controller 230 can be configured to determine/calculate, for example, fuel quality issues, a filter condition of a fuel filter (e.g., a fuel/water separator), and adherence to preventative maintenance processes of the fuel system 212 of the generator set 200 based on the values transmitted by the ECU 220 and data from, for example, a WIF sensor (e.g., the WIF sensor 316 shown in FIG. 3).

It will be appreciated that in some embodiments, the prime mover condition data is not required to be obtained by the ECU 220 and can be obtained by one or more sensors of the generator set 200.

The memory unit 235 can be configured to store one or more pre-entered processes. The one or more processes may be entered by an operator through the operator interface 236. Or the one or more processes may be entered into the memory unit 235 during a manufacturing process of the controller panel 270. The one or more processes can contain various ranges and thresholds that can be set, for example, by an operator or a manufacturer. The microprocessor of the genset controller 230 can be configured to monitor for and detect fuel quality issues, a filter condition of a fuel filter (e.g., a fuel/water separator), and adherence to preventative maintenance processes of the fuel system 212 of the generator set 200. For example, FIG. 4 illustrates one embodiment of a method for monitoring fuel quality of the generator set 200 run by the microprocessor. In another example, FIG. 5 illustrates one embodiment of a method for monitoring service level run by the microprocessor. A detailed example of the fuel system 212 is provided below with respect to FIG. 3, according to one embodiment.

Figure 3:
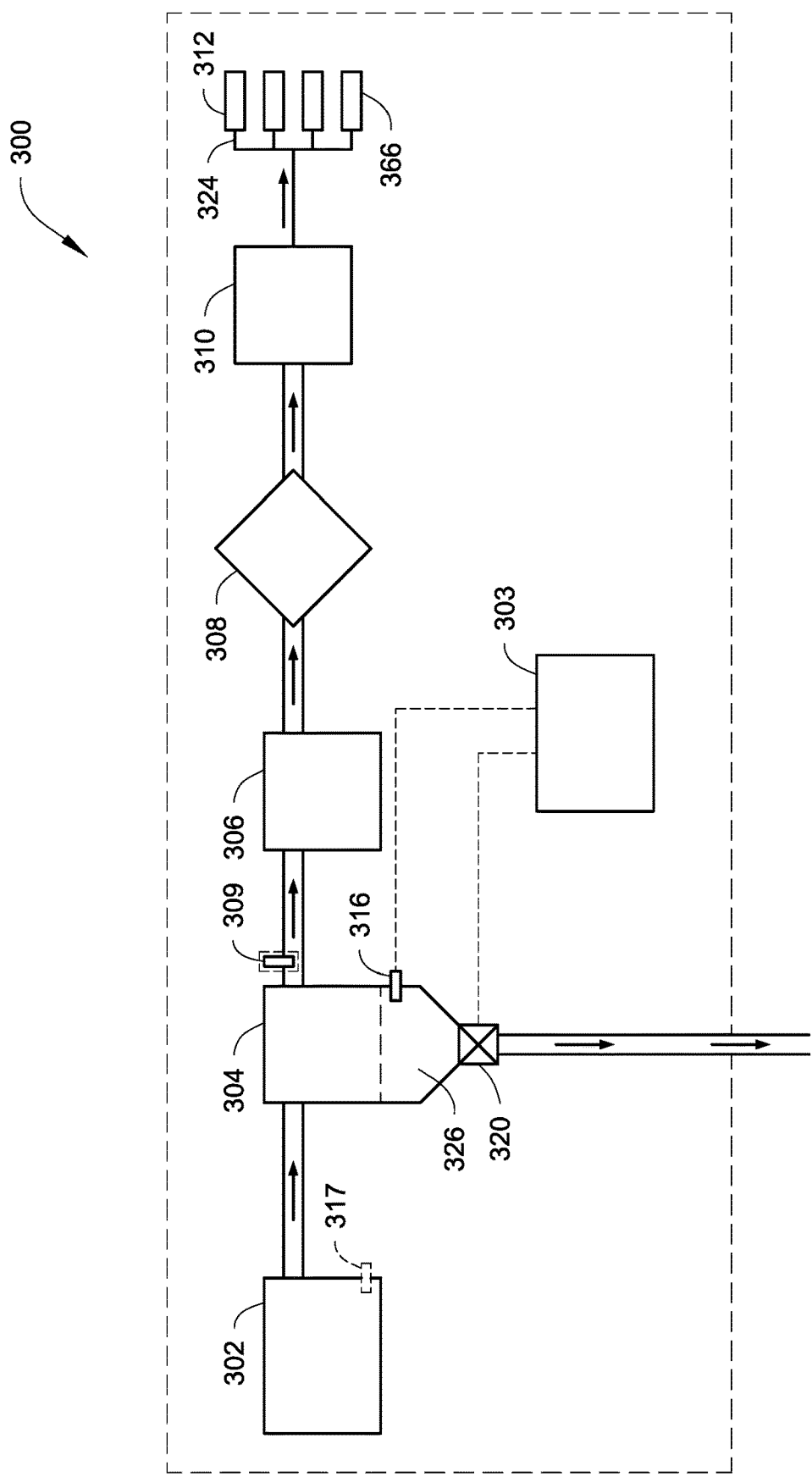
FIG. 3 is a schematic diagram of a fuel system of a power system, according to one embodiment.
Figure 4:
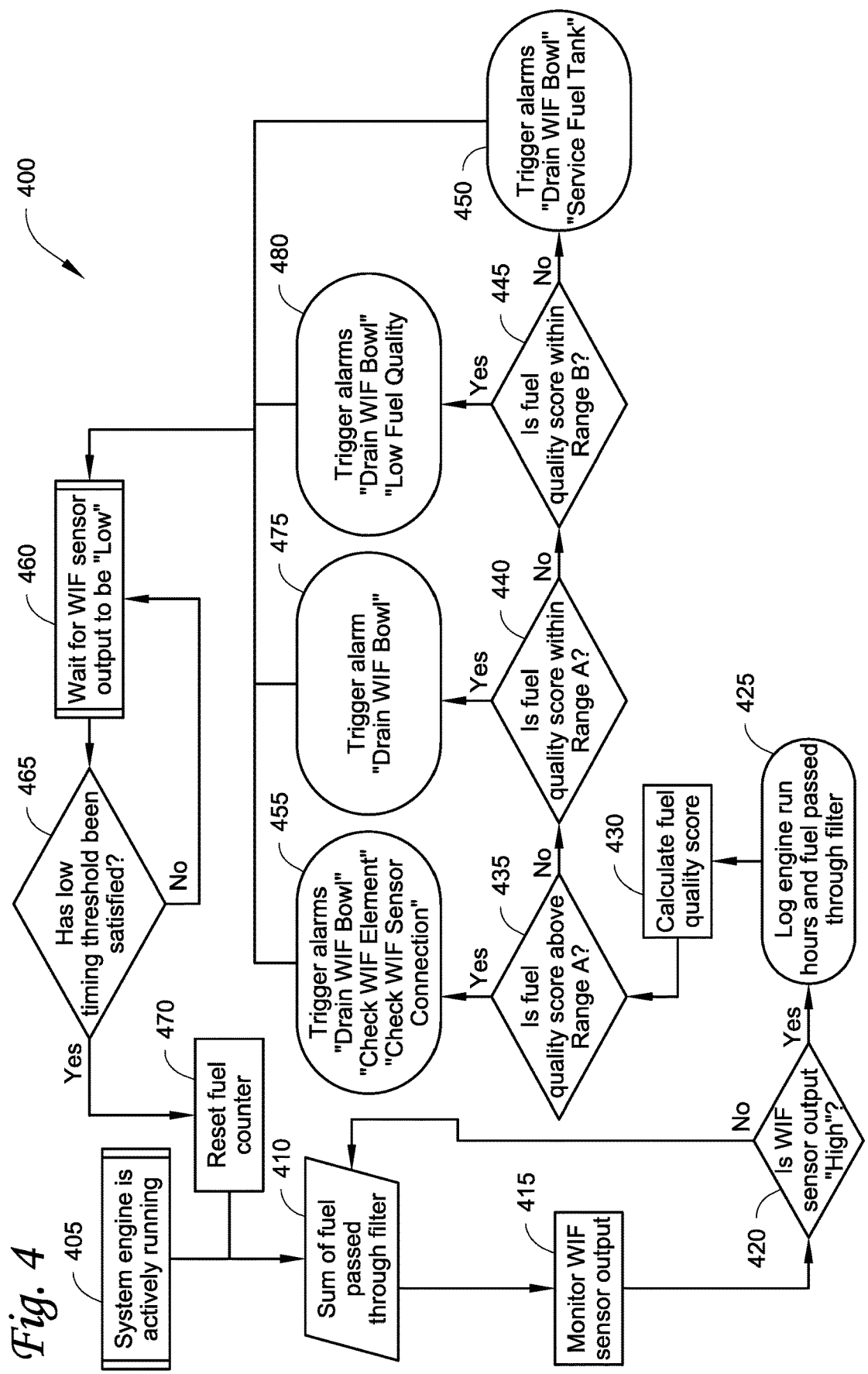
FIG. 4 is a flowchart of a method for monitoring fuel quality of a power system, according to one embodiment.

FIG. 3 shows a schematic of one embodiment of a fuel system 300 (e.g., the fuel system 212 shown in FIG. 2) for providing fuel to a common rail prime mover. Fuel (e.g., diesel fuel) may be supplied a fuel tank 302. The amount of fuel in the fuel tank 302 can be measured, using, for example, a mechanical float gauge (not shown). In some embodiments, the fuel system 300 can include an optional fuel tank sensor 317 that can measure a fuel amount in fuel tank 302 and communicate the measured fuel amount to, for example, a transport climate control system controller (not shown), a third party telematics device, a controller 303 (e.g., the genset controller 230 shown in FIG. 2), etc. The fuel travels from fuel tank 302 to a fuel/water separator 304 where water-based fluid (including, for example, free water and emulsified water) may be separated from the fuel to prevent said water-based fluid from being injected into the prime mover. The separated fuel may then exit the fuel/water separator and travel to supply pump 306. The fuel may then pass through another filter 308. The order of filtering and water separating may be interchanged. Filtered fuel is then pumped via injection pump 310 into a fuel rail 324. A fuel rail 324 may distribute fuel to a set of fuel injectors 312. Four fuel injectors are shown in FIG. 3; however, there may be any number depending on the number of cylinders required by the prime mover (e.g., the prime mover 210 shown in FIG. 2). A fuel injector 366 may inject fuel into a combustion chamber of the prime mover.

In some embodiments, the fuel system 300 can include a fuel amount sensor 309 that can monitor the amount of fuel directed from the fuel tank 302 through the water/fuel separator 304 and all the way to the fuel rail 324. The optional fuel amount sensor 309 can send a signal to a controller 303 indicative of the amount of fuel passing through the fuel system 300 (e.g., from the fuel tank 302 through fuel/water separator 304 and to ultimately to the fuel rail 324). While the optional fuel amount sensor 309 is shown in FIG. 3 as disposed between the fuel/water separator 304, it will be appreciated that in other embodiments the optional fuel amount sensor 309 can be disposed anywhere between the fuel/water separator 304 and the fuel rail 324. Also, in some embodiments the optional fuel amount sensor 309 can be positioned before the fuel/water separator 304. In these embodiments, the measured flow from the optional fuel amount sensor 309 would be a total flow amount instead of a filtered fuel (e.g., fuel without water separated by the fuel/water separator 304) directed to the fuel rail 324.

Returning to the fuel/water separator 304, the separated water-based fluid (herein referred to as water) may drain into a water collection reservoir 326 at the bottom of the fuel/water separator. It will be appreciated that the volume of the water collection reservoir 326 is known and constant. The fuel/water separator 304 may further include a water-in-fuel (WIF) sensor 316 to detect the amount of water in the water collection reservoir 326. The WIF sensor 316 may be any suitable sensor (e.g., optical, thermal, or electric conductivity, etc.) and may be, for example, coupled to an inner surface of water collection reservoir 326. In some embodiments, the WIF sensor 316 may be positioned at a threshold level that corresponds to a pre-determined threshold volume of water that has been separated from the fuel system. The threshold level may be pre-determined so as to correspond to, for example, a volume of fluid beyond which the probability of introducing water into the high pressure fuel system on the prime mover (with the fuel) is significantly increased. As such, if water is introduced with the fuel, fuel system degradation may result. Thus, the WIF sensor 316 can indicate when a threshold level of water has accumulated in the reservoir 326, so that a controller 303 can take actions to reduce degradation to the fuel system and/or prime mover. For example, when the sensor detects that a threshold level of water has been reached or exceeded, a raw voltage signal may be produced by the sensor 316 indicating a water-in-fuel condition. This signal may be received by the controller 303, indicating that water should be drained from the water collection reservoir 326. For example, in some embodiments, the WIF sensor 316 can output a "low" signal when the threshold level of water has not accumulated in the water collection reservoir 326 and can output a "high" signal when the threshold level of water has accumulated in the water collection reservoir 326.

Water may be drained from the water collection reservoir 326 via a valve 320. In some embodiments, the valve 320 can be, for example, an electronically controlled transfer valve, a manual drain valve, etc. In some embodiments, the valve 320 can be manually or automatically opened when the prime mover is off.

FIG. 4 illustrates a flowchart of a method 400 for monitoring fuel quality of a power system (e.g., the generator set 200 shown in FIG. 2), according to a first embodiment. The method 400 monitors fuel quality while a prime mover (e.g., the prime mover 210) of the power system is actively running. The method 400 begins at 405 whereby a controller of the power system (e.g., the controller 270, 303 shown in FIGS. 2 and 3) waits until the prime mover is actively running. A prime mover is actively running when the prime mover is operating under a stable running condition. That is, the prime mover is not in an initial startup phase and has been continuously running. In some embodiments, the controller can determine that the prime mover is not in an initial startup phase and has been continuously running by monitoring, for example, a RPM of the prime mover. For example, the controller can determine that the prime mover is continuously running when the RPM of the prime mover is above a RPM threshold (e.g., over 1450 RPM) The method 400 then proceeds to 410.

At 410, the controller determines the amount of fuel having passed through a fuel/water separator (e.g. the fuel/water separator 304 shown in FIG. 3) towards the fuel rail 324 over a set period of time. In some embodiments, the flow amount can be obtained from, for example, an ECU (e.g., the ECU 220 shown in FIG. 2) of the prime mover that is in communication with the controller. For example, as the flow amount through the fuel/water separator has been found to be directly proportional to a speed (e.g., RPM) of the prime mover, the controller can determine the flow amount by obtaining prime mover run hours (for example, the number of prime mover run hours while the prime mover is operating at a first non-zero speed and the number of prime mover run hours while the prime mover is operating at a second non-zero speed) from the ECU since the last time the WIF sensor was reset after indicating that the threshold level of water had accumulated in the water collection reservoir. In another example, the controller can determine the flow amount by receiving an amount of time an injection pump (e.g., the injection pump 310 shown in FIG. 3) has been running from the ECU, when the injection pump is a constant displacement injection pump. In some embodiments, the amount of fuel passing through the fuel/water separator can be obtained by a fuel amount sensor (e.g., the fuel amount sensor 309 shown in FIG. 3). In some embodiments, the amount of fuel passing through the fuel/water separator can be obtained by determining an injection quantity/fuel consumption. For example, when the prime mover is a common rail prime mover (e.g., a prime mover with electronically controlled injectors) the ECU can calculate and report a fuel consumption of the prime mover. The ECU can calculate fuel consumption based on a measured fuel pressure and a controlled injector open time When the injection quantity is used to determine the amount of fuel passing through the fuel/water separator it can be assumed that all fuel filtered by the fuel/water separator is used by the prime mover.

For example, in one embodiment, the amount of fuel having passed through the fuel/water separator 304 can be calculated by the formula:

total volume through fuel/water separator=sum of time at each RPM×flowrate at each RPM The controller can, for example, monitor the amount of time the prime mover is operating at a first speed (e.g., 1800 RPM) and the amount of time that the prime mover is operating at a second speed (e.g., 1500 RPM). That is, the controller can start a timer when, for example, the prime mover is operating at the first speed and can stop the timer when, for example, the prime mover is no longer operating at the first speed (e.g., switched to the second speed or turned off). The amount of time that the prime mover is operating at the first speed can then be multiplied by the flowrate at that speed. This calculation can be performed for each speed condition, and the results summated to provide the total volume through the fuel/water separator 304.

In another embodiment, when the injection pump is a constant displacement injection pump, the amount of fuel having passed through the fuel/water separator 304 can be calculated by the formula:

Total volume through fuel/water separator=sum of injection pump on time×flowrate In yet another embodiment, the amount of fuel having passed through the fuel/water separator 304 can be calculated by the formula:

Total volume through fuel/water separator=volume reported by a flow meter

In another embodiment, the amount of fuel having passed through the fuel/water separator 304 can be calculated by the formula:

Total volume through fuel/water separator=injection quantity as reported by the ECU Also, in some other embodiments, the amount of fuel having passed through the fuel water separator 304 can be calculated using the fuel tank sensor 317 in the fuel tank 302. In particular, the fuel level in the fuel tank 302 can be evaluated over time to determine the amount of fuel passing through the fuel/water separator 304.

The method 400 then proceeds to 415.

At 415, the controller monitors output from a WIF sensor (e.g., the WIF sensor 316 shown in FIG. 2) indicating the amount of water accumulated in a water collection reservoir of the fuel/water separator (e.g., the water collection reservoir 326 of the fuel/water separator 304 shown in FIG. 3). The method 400 the proceeds to 420.

At 420, when the controller determines whether the amount of water that has accumulated in the water collection reservoir of the fuel/water separator is above a threshold level based on the output of the WIF sensor, the method 400 proceeds to 425. It will be appreciated that the threshold level can vary and be based on the size of the water collection reservoir. When the controller determines that the amount of water that accumulated in the water collection reservoir of the fuel/water separator is below the threshold level based on the output of the WIF sensor, the method 400 proceeds back to 410.

At 425, the controller stores a value indicating the number of prime mover run hours since the last time the output of the WIF sensor indicated that the threshold level of water accumulated in the water collection reservoir has been reached. The controller also stores a value indicating the amount of fuel having passed through the fuel/water separator determined at 410. The method 400 then proceeds to 430.

At 430, the controller calculates a fuel quality score based on the values stored at 425. That is, the controller calculates the fuel quality score based on the number of prime mover run hours since the last time the output of the WIF sensor indicated that the threshold level of water accumulated in the water collection reservoir had been reached and based on the amount of fuel having passed through the fuel/water separator. Based on the flow amount and the number of prime mover run hours, the controller can determine a flowrate of the fuel through the fuel/water separator. The controller can calculate the fuel quality score by correlating the amount of fuel passing through the fuel/water separator with the amount of time since the water collection reservoir was last drained (e.g., a drainage interval). The controller can compare the amount of fuel passing through the fuel/water separator to a known volume of the water collection reservoir to determine the fuel quality score.

For example, in one embodiment the fuel quality score can be calculated by the formula:

Fuel quality score=Total filtered volume/WIF bowl volume

The method 400 then proceeds to 435.

At 435, the controller determines whether the fuel quality score calculated at 430 is above a range A. In one embodiment, the range A can be defined as resulting from a water content in the fuel between, for example, ~10 and ~200 parts per million (ppm) by volume. In this embodiment, the controller can determine whether the fuel quality score reflects a water content in the fuel of less than, for example, ~10 ppm.

When the controller determines that the calculated fuel quality score is above range A, the method 400 proceeds to 455. When the controller determines that the calculated fuel quality score is not above range A, the method 400 proceeds to 440.

At 440, the controller determines whether the fuel quality score calculated at 430 is within the range A. For example, the controller can determine whether the fuel quality score reflects a water content in the fuel of between, for example, ~10 and ~200 ppm. When the controller determines that the calculated fuel quality score is within the range A, the method 400 proceeds to 475. When the controller determines that the calculated fuel quality score is not within the range A, the method 400 proceeds to 445.

At 445, the controller determines whether the fuel quality score calculated at 430 is within a range B. In one embodiment, the range B can be defined as resulting from a water content in the fuel between, for example, ~200 and ~1000 ppm by volume. Accordingly, the controller can determine whether the fuel quality score reflects a water content in the fuel of between, for example, ~200 and ~1000 ppm. When the controller determines that the calculated fuel quality score is within the range B, the method 400 proceeds to 480. When the controller determines that the calculated fuel quality score is not within the range B, the method 400 proceeds to 450.

At 455, the controller has determined that the calculated fuel quality score is above range A and therefore has very little water mixed in the fuel (e.g., less than ~10 ppm). For example, if the WIF sensor is configured to trigger when the volume in the water collection reservoir reaches 180 mL, a total flowed volume of fuel passing through the fuel/water separator is at or above ~4755 gallons That is, the controller has determined that the water collection reservoir is filling too slowly based on the amount of fuel being used to be trustworthy. Accordingly, the controller determines that the low amount of water in the fuel is impractical and there may be an error in the fuel system (e.g., a damaged separation membrane of the fuel/water separator; a disconnected WIF sensor; a damaged WIF sensor; etc.). The controller is configured to trigger multiple alerts including an alert to drain the water collection reservoir, an alert to check the water collection reservoir, an alert to check the WIF sensor, and an alert to check the WIF sensor connection to the controller. The alerts can be, for example, sent to an operator via a text message from the controller, displayed on a display on the controller, reported to a website through a telematics device, etc. In some embodiments, the alerts can be recorded in a datalogger. The method 400 then proceeds to 460.

At 475, the controller has determined that the calculated fuel quality score is within the range A and therefore has an acceptable amount of water mixed in the fuel (e.g., between ~10 and ~200 ppm). For example, if the WIF sensor is configured to trigger when the volume in the water collection reservoir reaches 180 mL, a total flowed volume of fuel passing through the fuel/water separator is between ~237 gallons and ~4755 gallons That is, the controller determines that the amount of water in the fuel is within an acceptable range and acceptable for use. Accordingly, the controller is configured to trigger an alert to drain the water collection reservoir to continue proper operation of the power system. In some embodiments, the alerts can be recorded in a datalogger. The method 400 then proceeds to 460.

At 480, the controller has determined that the calculated fuel quality score is within the range B and therefore has an unacceptable amount of water mixed in the fuel (e.g., between ~200 and ~1000 ppm). For example, if the WIF sensor is configured to trigger when the volume in the water collection reservoir reaches 180 mL, a total flowed volume of fuel passing through the fuel/water separator is between ~47 gallons and ~237 gallons. That is, the controller determines that the quality of the fuel being used may not be acceptable. Accordingly, the controller is configured to trigger multiple alerts including an alert to drain the water collection reservoir, and an alert indicating low quality fuel is being used by the prime mover. In some embodiments, the alerts can be recorded in a datalogger. The method 400 then proceeds to 460.

At 450, the controller has determined that the calculated fuel quality score is below the range B and therefore has an excessive amount of water mixed in the fuel (e.g., more than ~1000 ppm). For example, if the WIF sensor is configured to trigger when the volume in the water collection reservoir reaches 180 mL, a total flowed volume of fuel passing through the fuel/water separator is less than ~47 gallons. That is, the controller determines that the high amount of water in the fuel indicative of separated water in the fuel tank and/or an unmaintained fuel tank. Accordingly, the controller is configured to trigger multiple alerts including an alert to drain the water collection reservoir, and an alert to service the fuel tank (e.g., drain water contained in the fuel tank). In some embodiments, the alerts can be recorded in a datalogger. The method 400 then proceeds to 460.

At 460, the controller continues to monitor output from the WIF sensor until the controller determines that the amount of water accumulated in the water collection reservoir of the fuel/water separator is below the threshold level. Once the controller determines that the amount of water accumulated in the water collection reservoir is below the threshold level, the method 400 proceeds to 465.

At 465, the controller waits until a time threshold, for the amount of time that the water accumulated in the water collection reservoir is below the threshold level, has been satisfied. The time threshold is set to a period of time to provide hysteresis to take into account, for example, fuel sloshing that can occur while the power system is in transport and thereby provide an output of the WIF sensor indicating that the amount of water in the water collection reservoir is above the threshold level. The time threshold can be dependent on whether the method 400 is proceeding to 465 from 450, 455, 475 or 480. For example, when the method 400 proceeds to 465 from one of 455, 475 and 480, the time threshold can be about 15 minutes. When the method 400 proceeds to 464 from 450, the time threshold can be about 5 minutes or lower (e.g., about 1 minute).

By providing a time threshold, the method 400 can prevent false triggering that the output of the WIF sensor is above the threshold level during transport. When the controller determines that the timing threshold has been satisfied, the method 400 proceeds to 470. When the controller determines that the timing threshold has not been satisfied, the method 400 proceeds back to 460 to wait until the output of the WIF sensor is below the threshold level.

At 470, the controller resets a fuel counter that can is used to assist in tracking fuel use over a set period of time. The method 400 then proceeds back to 410.

FIG. 5 illustrates a flowchart of a method 500 for monitoring service level of a power system (e.g., the generator set 200 shown in FIG. 2), according to one embodiment. The method 500 occurs during a pre-trip test of the power system (e.g., while a prime mover (e.g., the prime mover 210) of the power system is not actively running) and can evaluate data outputted by a WIF sensor (e.g., the WIF sensor 316 shown in FIG. 3) with respect to a last recorded pre-trip test report and determine a service level of the power system. The method 500 begins at 505 whereby a controller of the power system (e.g., the controller 270, 303 shown in FIGS. 2 and 3) is powered on. The method 500 then proceeds to 510.

At 510, the controller monitors output from the WIF sensor indicating the amount of water accumulated in a water collection reservoir of a fuel/water separator (e.g., the water collection reservoir 326 of the fuel/water separator 304 shown in FIG. 3). The method 500 the proceeds to 515.

At 515, the controller determines whether the amount of water that has accumulated in the water collection reservoir of the fuel/water separator is at or above a threshold level based on the output of the WIF sensor. When the controller determines that the amount of water that has accumulated in the water collection reservoir of the fuel/water separator is below the threshold level based on the output of the WIF sensor, the method 500 proceeds to 520. When the controller determines that the amount of water that has accumulated in the water collection reservoir of the fuel/water separator is at or above the threshold level based on the output of the WIF sensor, the method 500 proceeds to 525. It will be appreciated that the threshold level can vary and be based on the size of the water collection reservoir.

At 520, the controller determines whether a pre-trip test of the power system has been run by the user. A pre-trip test can be a test run by the controller for a brief period of time while the power system is operating that checks if any alarm conditions are found. In some embodiments, the controller can include an event logger that records each time a pre-trip test is run. If a pre-trip has been run, the method proceeds to 530. If a pre-trip test has not been run, the method proceeds to 550.

At 530, the controller determines and stores a value indicating the number of prime mover run hours since the last pre-trip test. The number of prime mover run hours since the last pre-trip test can be used as a timestamp for when a subsequent alarm code is generated at 540. The method 500 then proceeds to 535.

At 535, the controller monitors an updated output from the WIF sensor and determines whether the amount of water that has accumulated in the water collection reservoir of the fuel/water separator is at or above the threshold level based on the output of the WIF sensor. When the controller determines that the amount of water that has accumulated in the water collection reservoir of the fuel/water separator is at or above the threshold level based on the output of the WIF sensor, the method 500 proceeds to 540. When the controller determines that the amount of water that has accumulated in the water collection reservoir of the fuel/water separator is below the threshold level based on the output of the WIF sensor, the method 500 proceeds to 545.

At 540, the controller has determined that there is an issue with the fuel system (e.g., during the pre-trip test, the water collection reservoir is nearly full and has reached a level in which the WIF sensor is triggered as the amount of water in the water collection reservoir has reached a threshold level; an empty water collection reservoir is rapidly filled thus requiring a fuel tank check or a faulty WIF sensor check). That is, the controller determines that the high amount of water in the fuel upon pre-trip testing indicates that there is an issue with the fuel system. Accordingly, the controller is configured to trigger multiple alerts including an alert to drain the water collection reservoir, an alert to check the WIF sensor, and an alert to check the water collection reservoir. In some embodiments, the alerts can be recorded in a datalogger. The method 500 can then proceed to 405 in FIG. 4 or can return to 505 when the power system is restarted.

At 545, the controller determines that no conclusion can be made and logs this information into a datalogger. The controller is configured to log and store the number of prime mover hours accumulated since the last shutdown of the power system. The method then proceeds to 405 in FIG. 4 or can return to 505 when the power system is restarted.

At 550, the controller is configured to determine whether the power system has transitioned into actively running. As discussed above with respect to FIG. 4, a prime mover is actively running when the prime mover is operating under a stable running condition. If the controller determines that the power system has transitioned into actively running, the method 500 proceeds to 555. If the controller determines that the power system has not transitioned into actively running, the method 500 proceeds to 560.

At 555, the controller has determined that the power system has not undergone a pre-trip test prior to actively running. Accordingly, the controller is configured to trigger an alert that the power system is running without a pre-trip test. In some embodiments, the alerts can be recorded in a datalogger. The method 500 can then proceed to 405 in FIG. 4 or can return to 505 when the power system is restarted.

At 560, the controller determines that no conclusion can be made and logs this information into a datalogger. In some embodiments, the controller can determine, for example, that the power system has been turned on and then immediately off. The method 500 can remain at 560 until the controller determines that the prime mover has started at which point the method 500 can proceed to 555.

At 525, the controller the controller determines whether a pre-trip test of the power system has been run by the user. A pre-trip test can be a test run by the controller for a brief period of time while the power system is operating that checks if any alarm conditions are found. In some embodiments, the controller can include an event logger that records each time a pre-trip test is run. If a pre-trip has been run, the method proceeds to 565. If a pre-trip test has not been run, the method proceeds to 585.

At 565, the controller determines and stores a value indicating the number of prime mover run hours since the last pre-trip test. The number of prime mover run hours since the last pre-trip test can be used as a timestamp for when a subsequent alarm code is generated at 575 or can be used as a reset time at 470 in FIG. 4. The method 500 then proceeds to 570.

At 570, the controller monitors an updated output from the WIF sensor and determines whether the amount of water that has accumulated in the water collection reservoir of the fuel/water separator is at or above the threshold level based on the output of the WIF sensor. When the controller determines that the amount of water that has accumulated in the water collection reservoir of the fuel/water separator is at or above the threshold level based on the output of the WIF sensor, the method 500 proceeds to 575. When the controller determines that the amount of water that has accumulated in the water collection reservoir of the fuel/water separator is below the threshold level based on the output of the WIF sensor, the method 500 proceeds to 580.

At 575, the controller has determined that there is an issue with the fuel system. That is, the controller determines that the high amount of water in the fuel upon pre-trip testing indicates that there is an issue with the fuel system. Accordingly, the controller is configured to trigger multiple alerts including an alert noting an unmaintained power system, and an alert to check the WIF sensor. The method 500 can then proceed to 405 in FIG. 4 or can return to 505 when the power system is restarted.

At 580, the controller determines that the water collection reservoir of the fuel/water container has been drained and stores a value indicating the number of prime mover run hours since the last time the water collection reservoir was drained. The method 500 can then proceed to 405 in FIG. 4.

At 585, the controller is configured to determine whether the power system has transitioned into actively running. As discussed above with respect to FIG. 4, a prime mover is actively running when the prime mover is operating under a stable running condition. If the controller determines that the power system has transitioned into actively running, the method 500 proceeds to 590. If the controller determines that the power system has not transitioned into actively running, the method 500 proceeds to 595.

At 590, the controller has determined that the power system has not undergone a pre-trip test prior to actively running. Accordingly, the controller is configured to trigger an alert of an unmaintained power system. The controller is also configured to store data indicating that the power system is running without a pre-trip test. The method 500 can then proceed to 405 in FIG. 4 or can return to 505 when the power system is cycled off then back on.

At 595, the controller determines that no conclusion can be made and the controller can determine that no conclusion can be made. In some embodiments, the controller can determine, for example, that the power system has been turned on and then immediately off. The method 500 can remain at 595 until the controller determines that the prime mover has started at which point the method 500 can proceed to 590.

Aspects:

It is noted that any of aspects 1-10, any one of aspects 11-20, and aspect 21 can be combined.

Aspect 1. A method for monitoring fuel quality of a power system used in transport, the method comprising:
- a controller of the power system determining that the prime mover is actively running;
- the controller monitoring an output of a water-in-fuel (WIF) sensor configured to measure an amount of water accumulated in a water collection reservoir of a fuel/water separator that separates water from fuel passing there through;
- the controller determining an amount of fuel passing through the fuel/water separator;
- the controller calculating a fuel quality score of the fuel based on the output of the WIF sensor and the amount of fuel having passed through the fuel/water separator; and
- the controller triggering different alerts based on the calculated fuel quality score.

Aspect 2. The method of aspect 1, further comprising the controller calculating the fuel quality score upon the output of the WIF sensor indicating that a threshold level of water has accumulated in the water collection reservoir.

Aspect 3. The method of any one of aspects 1 and 2, wherein determining the amount of fuel passing through the fuel/water separator includes the controller receiving prime mover run hours from an engine control unit (ECU) of the prime mover, and the controller determining the amount of fuel passing through the fuel/water separator based on the prime mover run hours received from the ECU.

Aspect 4. The method of any one of aspects 1-3, wherein determining the amount of fuel passing through the fuel/water separator includes the controller receiving an amount of time an injection pump has been running from an engine control unit (ECU) of the prime mover, and the controller determining the amount of fuel passing through the fuel/water separator based on the amount of time the injection pump had been running received from the ECU.

Aspect 5. The method of any one of aspects 1-4, wherein determining the amount of fuel passing through the fuel/water separator includes the controller receiving a direct flow rate measurement from a sensor of the fuel system, and the controller determining the amount of fuel passing through the fuel/water separator based on the direct flow rate measurement received from the sensor.

Aspect 6. The method of any one of aspects 1-5, wherein determining the amount of fuel passing through the fuel/water separator includes the controller receiving an injection quantity value from an engine control unit (ECU) of the prime mover, and the controller determining the amount of fuel passing through the fuel/water separator based on the injection quantity value received from the ECU.

Aspect 7. The method of any one of aspects 1-6, further comprising the controller triggering an alert to check the water collection reservoir, an alert to check the WIF sensor, and an alert to check the WIF sensor connection to the controller when the fuel quality score is above a first fuel score range.

Aspect 8. The method of any one of aspects 1-7, further comprising the controller triggering an alert to drain the water collection reservoir when the fuel quality score is within a first fuel score range.

Aspect 9. The method of any one of aspects 1-8, further comprising the controller triggering an alert to indicate low quality fuel when the fuel quality score is within a second fuel score range.

Aspect 10. The method of any one of aspects 1-9, further comprising the controller triggering an alert to service the fuel tank when the fuel quality score is below a second fuel score range.

Aspect 11. A power system for use in transport, the power system comprising:
- a fuel system that includes:
  - a fuel tank for storing fuel,
  - a fuel/water separator configured to separate water from the fuel as the fuel is being directed to a prime mover of the power system, wherein the fuel/water separator includes a water collection reservoir configured to collect water separated from the fuel by the fuel/water separator, and
  - a water-in-fuel (WIF) sensor configured to measure an amount of the water accumulated in the water collection reservoir;
- a prime mover configured to receive fuel downstream of the fuel/water separator; and
- a controller configured to control operation of the power system including a speed of the prime mover, wherein the controller is configured to:
  - determine that the prime mover is actively running,
  - monitor an output of the WIF sensor,
  - determine an amount of fuel passing through the fuel/water separator,
  - calculate a fuel quality score of the fuel based on the output of the WIF sensor and the amount of fuel having passed through the fuel/water separator, and
  - trigger different alerts based on the calculated fuel quality score.

Aspect 12. The power system of aspect 11, wherein the controller is configured to calculate the fuel quality score upon the output of the WIF sensor indicating that a threshold level of water has accumulated in the water collection reservoir.

Aspect 13. The power system of any one of aspects 11 and 12, wherein, in order to determine the amount of fuel passing through the fuel/water separator, the controller is configured to:
- receive prime mover run hours from an engine control unit (ECU) of the prime mover, and
- determine the amount of fuel passing through the fuel/water separator based on the prime mover run hours received from the ECU.

Aspect 14. The power system of any one of aspects 11-13, wherein, in order to determine the amount of fuel passing through the fuel/water separator, the controller is configured to:
- receive an amount of time an injection pump has been running from an engine control unit (ECU) of the prime mover, and
- determine the amount of fuel passing through the fuel/water separator based on the amount of time the injection pump had been running received from the ECU.

Aspect 15. The power system of any one of aspects 11-14, wherein, in order to determine the amount of fuel passing through the fuel/water separator, the controller is configured to:
- receive a direct flow rate measurement from a sensor of the fuel system, and determine the amount of fuel passing through the fuel/water separator based on the direct flow rate measurement received from the sensor.

Aspect 16. The power system of any one of aspects 11-15, wherein, in order to determine the amount of fuel passing through the fuel/water separator, the controller is configured to:
receive an injection quantity value from an engine control unit (ECU) of the prime mover, and
determine the amount of fuel passing through the fuel/water separator based on the injection quantity value received from the ECU.

Aspect 17. The power system of any one of aspects 11-16, wherein the controller is configured to: trigger an alert to check the water collection reservoir, an alert to check the WIF sensor, and an alert to check the WIF sensor connection to the controller when the fuel quality score is above a first fuel score range.

Aspect 18. The power system of any one of aspects 11-17, wherein the controller is configured to trigger an alert to drain the water collection reservoir when the fuel quality score is within a first fuel score range.

Aspect 19. The power system of any one of aspects 11-18, wherein the controller is configured to trigger an alert to indicate low quality fuel when the fuel quality score is within a second fuel score range.

Aspect 20. The power system of any one of aspects 11-19, wherein the controller is configured to trigger an alert to service the fuel tank when the fuel quality score is below a second fuel score range.

Aspect 21. A method for monitoring a service level of a power system used in transport, the method comprising:
a controller of the power system determining that the prime mover has been powered on;
the controller monitoring an output of a water-in-fuel (WIF) sensor configured to measure an amount of water accumulated in a water collection reservoir of a fuel/water separator that separates water from fuel passing there through;
the controller waiting a predetermined time period after monitoring the output of the WIF sensor;
after the predetermined time period, the controller determining whether a pre-trip test has been run and obtaining an updated output of the WIF sensor; and
the controller triggering an alert based on the whether the pre-trip test has been urn and the updated output of the WIF sensor.

The terminology used in this Specification is intended to describe particular embodiments and is not intended to be limiting. The terms "a," "an," and "the" include the plural forms as well, unless clearly indicated otherwise. The terms "comprises" and/or "comprising," when used in this Specification, specify the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts without departing from the scope of the present disclosure. This Specification and the embodiments described are exemplary only, with the true scope and spirit of the disclosure being indicated by the claims that follow.

What is claimed is:

1. A method for monitoring fuel quality of a power system used in transport, the method comprising:
a controller of the power system determining that the prime mover is actively running;
upon determining that the prime mover is actively running, the controller determining an amount of fuel passing through the fuel/water separator;
while the prime mover is actively running, the controller monitoring an output of a water-in-fuel (WIF) sensor configured to indicate when a threshold amount of water has accumulated in a water collection reservoir of a fuel/water separator that separates water from fuel passing there through;
while the prime mover is actively running, the controller calculating a fuel quality score of the fuel based on the output of the WIF sensor and the amount of fuel having passed through the fuel/water separator; and
while the prime mover is actively running, the controller triggering different alerts based on the calculated fuel quality score.

2. The method of claim 1, further comprising the controller calculating the fuel quality score upon the output of the WIF sensor indicating that a threshold level of water has accumulated in the water collection reservoir.

3. The method of claim 1, wherein determining the amount of fuel passing through the fuel/water separator includes the controller receiving prime mover run hours from an engine control unit (ECU) of the prime mover, and the controller determining the amount of fuel passing through the fuel/water separator based on the prime mover run hours received from the ECU.

4. The method of claim 1, wherein determining the amount of fuel passing through the fuel/water separator includes the controller receiving an amount of time an injection pump has been running from an engine control unit (ECU) of the prime mover, and the controller determining the amount of fuel passing through the fuel/water separator based on the amount of time the injection pump had been running received from the ECU.

5. The method of claim 1, wherein determining the amount of fuel passing through the fuel/water separator includes the controller receiving a direct flow rate measurement from a sensor of the fuel system, and the controller determining the amount of fuel passing through the fuel/water separator based on the direct flow rate measurement received from the sensor.

6. The method of claim 1, wherein determining the amount of fuel passing through the fuel/water separator includes the controller receiving an injection quantity value from an engine control unit (ECU) of the prime mover, and the controller determining the amount of fuel passing through the fuel/water separator based on the injection quantity value received from the ECU.

7. The method of claim 1, further comprising the controller triggering an alert to check the water collection reservoir, an alert to check the WIF sensor, and an alert to check the WIF sensor connection to the controller when the fuel quality score is above a first fuel score range.

8. The method of claim 1, further comprising the controller triggering an alert to drain the water collection reservoir when the fuel quality score is within a first fuel score range.

9. The method of claim 1, further comprising the controller triggering an alert to indicate low quality fuel when the fuel quality score is within a low quality fuel score range.

10. The method of claim 1, further comprising the controller triggering an alert to service the fuel tank when the fuel quality score is below a low quality fuel score range.

11. A power system for use in transport, the power system comprising:
a fuel system that includes:
a fuel tank for storing fuel,
a fuel/water separator configured to separate water from the fuel as the fuel is being directed to a prime mover of the power system, wherein the fuel/water separator includes a water collection reservoir configured to collect water separated from the fuel by the fuel/water separator, and
a water-in-fuel (WIF) sensor configured to indicate when a threshold amount of the water has accumulated in the water collection reservoir;
a prime mover configured to receive fuel downstream of the fuel/water separator; and
a controller configured to control operation of the power system including a speed of the prime mover, wherein the controller is configured to:
determine that the prime mover is actively running,
upon determining that the prime mover is actively running, determine an amount of fuel passing through the fuel/water separator,
monitor an output of the WIF sensor while the prime mover is actively running,
calculate a fuel quality score of the fuel based on the output of the WIF sensor and the amount of fuel having passed through the fuel/water separator while the prime mover is actively running, and
trigger different alerts based on the calculated fuel quality score while the prime mover is actively running.

12. The power system of claim 11, wherein the controller is configured to calculate the fuel quality score upon the output of the WIF sensor indicating that a threshold level of water has accumulated in the water collection reservoir.

13. The power system of claim 11, wherein, in order to determine the amount of fuel passing through the fuel/water separator, the controller is configured to:
receive prime mover run hours from an engine control unit (ECU) of the prime mover, and
determine the amount of fuel passing through the fuel/water separator based on the prime mover run hours received from the ECU.

14. The power system of claim 11, wherein, in order to determine the amount of fuel passing through the fuel/water separator, the controller is configured to:
receive an amount of time an injection pump has been running from an engine control unit (ECU) of the prime mover, and
determine the amount of fuel passing through the fuel/water separator based on the amount of time the injection pump had been running received from the ECU.

15. The power system of claim 11, wherein, in order to determine the amount of fuel passing through the fuel/water separator, the controller is configured to:
receive a direct flow rate measurement from a sensor of the fuel system, and
determine the amount of fuel passing through the fuel/water separator based on the direct flow rate measurement received from the sensor.

16. The power system of claim 11, wherein, in order to determine the amount of fuel passing through the fuel/water separator, the controller is configured to:
receive an injection quantity value from an engine control unit (ECU) of the prime mover, and
determine the amount of fuel passing through the fuel/water separator based on the injection quantity value received from the ECU.

17. The power system of claim 11, wherein the controller is configured to: trigger an alert to check the water collection reservoir, an alert to check the WIF sensor, and an alert to check the WIF sensor connection to the controller when the fuel quality score is above a first fuel score range.

18. The power system of claim 11, wherein the controller is configured to trigger an alert to drain the water collection reservoir when the fuel quality score is within a first fuel score range.

19. The power system of claim 11, wherein the controller is configured to trigger an alert to indicate low quality fuel when the fuel quality score is within a low quality fuel score range.

20. The power system of claim 11, wherein the controller is configured to trigger an alert to service the fuel tank when the fuel quality score is below a low quality fuel score range.

* * * * *